US012805789B2

(12) United States Patent
Deno et al.

(10) Patent No.: US 12,805,789 B2
(45) Date of Patent: Nov. 24, 2026

(54) SYSTEM AND METHOD FOR ASSESSING CONDUCTION BLOCK IN TISSUE

(71) Applicant: St. Jude Medical, Cardiology Division, Inc., St. Paul, MN (US)

(72) Inventors: Don Curtis Deno, Andover, MN (US); Linda L. Ruetz, New Brighton, MN (US); Paul James Reed, Minneapolis, MN (US); Jeffrey A. Schweitzer, St. Paul, MN (US); Loell Boyce Moon, Ham Lake, MN (US); Scott Allen Hareland, Lino Lakes, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 258 days.

(21) Appl. No.: 18/606,036

(22) Filed: Mar. 15, 2024

(65) Prior Publication Data

US 2024/0306975 A1 Sep. 19, 2024

Related U.S. Application Data

(60) Provisional application No. 63/490,887, filed on Mar. 17, 2023.

(51) Int. Cl.

| | |
|---|---|
| ***A61B 5/367*** | (2021.01) |
| ***A61B 5/00*** | (2006.01) |
| ***A61B 5/287*** | (2021.01) |

(52) U.S. Cl.

CPC .............. *A61B 5/367* (2021.01); *A61B 5/287* (2021.01); *A61B 5/6858* (2013.01)

(58) Field of Classification Search

CPC ....... A61B 5/367; A61B 5/287; A61B 5/6858; A61B 2018/00267; A61B 2018/00357; A61B 2018/00577; A61B 2018/00666; A61B 2018/00839; A61B 18/1492; A61B 5/4836; A61B 5/361; A61N 1/37512

USPC .......................................... 600/509, 508, 450

See application file for complete search history.

(56) References Cited

U.S. PATENT DOCUMENTS

| | | | | |
|---|---|---|---|---|
| 9,277,872 B2 * | 3/2016 | Harlev | A61B 18/00 | |
| 9,662,033 B2 | 5/2017 | Severino | | |
| 2005/0119647 A1 * | 6/2005 | He | A61B 18/1492 606/41 | |
| 2009/0281541 A1 * | 11/2009 | Ibrahim | A61B 18/1492 606/42 | |
| 2017/0156791 A1 * | 6/2017 | Govari | A61B 5/287 | |
| 2018/0029611 A1 | 2/2018 | Gage et al. | | |
| 2018/0116539 A1 * | 5/2018 | Olson | A61B 5/287 | |
| 2018/0296111 A1 | 10/2018 | Deno et al. | | |

(Continued)

*Primary Examiner* — Tammie K Marlen
*Assistant Examiner* — Mary Grace Schlueter
(74) *Attorney, Agent, or Firm* — Wiley Rein LLP

(57) ABSTRACT

Conduction block across a lesion in tissue can be assessed by applying a pacing signal to tissue on one side of the lesion and sensing electrophysiological activity in the tissue on the opposite side of the lesion. A signal processor, such as may be incorporated into an electroanatomical mapping system, analyzes the sensed electrophysiological activity for a response evoked by the pacing signal and outputs an indicator of conduction block status. More particularly, when a preset number of consecutive pacing pulses do not yield an evoked response, an indicator of block can be output; conversely, when a preset number of consecutive pacing pulses do yield an evoked response, an indicator of no block can be output.

21 Claims, 6 Drawing Sheets

(56) References Cited

U.S. PATENT DOCUMENTS

| | | | |
|---|---|---|---|
| 2021/0038101 | A1 | 2/2021 | Wu et al. |
| 2021/0085387 | A1 | 3/2021 | Amit et al. |

* cited by examiner

SYSTEM AND METHOD FOR ASSESSING CONDUCTION BLOCK IN TISSUE

CROSS-REFERENCE TO RELATED APPLICATIONS

This application claims the benefit of U.S. provisional application No. 63/490,887, filed 17 Mar. 2023, which is hereby incorporated by reference as though fully set forth herein.

BACKGROUND

The present disclosure relates generally to electrophysiology procedures and the treatment of cardiac rhythm disorders including, but not limited to, atrial fibrillation. In particular, the present disclosure relates to systems, apparatuses, and methods for assessing the efficacy of ablation lesions created to interrupt abnormal conduction pathways.

Various cardiac rhythm disorders are known. Likewise, it is known that certain cardiac rhythm disorders can be treated by creating ablation lesions in the heart to interrupt abnormal conduction pathways that may be causing or contributing to the arrhythmia.

For example, it is understood that atrial fibrillation can result from disorganized electrical activity in the heart muscle. One well-known therapy for atrial fibrillation is the creation of lesions that isolate one or more of the pulmonary veins from the left atrium-a so called pulmonary vein isolation, or PVI, procedure.

Those of ordinary skill in the art will be familiar with various techniques that can be used to create PVI lesions. These include, without limitation, radiofrequency (RF) ablation, cryogenic ablation, microwave ablation, laser ablation, high intensity focused ultrasound (HIFU) ablation, and pulse field ablation (PFA) (also known as irreversible electroporation (IRE)).

Regardless of the technique used to create PVI lesions, practitioners often wish to verify that the lesions have had the desired effect of interrupting electrical conduction between the pulmonary vein(s) and the left atrium. "Exit block" refers to verifying that the lesions are preventing the propagation of conduction from the pulmonary veins to the left atrium, which conduction might sustain atrial fibrillation. "Entrance block" refers to the reverse-conduction from the left atrium back into the pulmonary veins. Achieving both exit block and entrance block is known as "complete block" or "bidirectional block."

Exit block can be tested by pacing tissue on the upstream (pulmonary vein) side of a PVI lesion and sensing electrophysiological activity on the downstream (left atrial) side of the PVI lesion. If the upstream pacing signal evokes a response on the downstream side of the PVI lesion, then exit block has not been achieved.

Known approaches to testing exit block, however, are manual and labor intensive. The practitioner must properly pace the upstream tissue and then interpret the electrophysiological signal sensed on the downstream side of the lesion. Thus, it could take several minutes before the practitioner is able to determine whether or not block has been achieved.

BRIEF SUMMARY

Disclosed herein is a method of assessing conduction block across a lesion in a tissue. The method includes: applying a pacing signal to the tissue on a first side of the lesion, wherein the pacing signal includes a plurality of pacing pulses; sensing electrophysiological activity in the tissue on a second side of the lesion, wherein the second side of the lesion is opposite the first side of the lesion; analyzing, in a signal processor, the sensed electrophysiological activity for a response evoked by the pacing signal; and outputting, via the signal processor, an indicator of conduction block status. The indicator of conduction block status can be an indicator of conduction block when a preset number of consecutive pacing pulses do not evoke the response; an indicator of no conduction block when the preset number of consecutive pacing pulses evoke the response; and an indicator of uncertain block status otherwise. The indicator of conduction block status can include a visual indicator of conduction block status; an audible indicator of conduction block status; and/or a haptic indicator of conduction block status.

In embodiments of the disclosure, the step of applying the pacing signal to the tissue on the first side of the lesion includes applying the pacing signal to the tissue using a first plurality of electrodes positioned on the first side of the lesion; and the step of sensing electrophysiological activity in the tissue on the second side of the lesion includes sensing the electrophysiological activity using a second plurality of electrodes positioned on the second side of the lesion. It is contemplated that the first plurality of electrodes and the second plurality of electrodes may be mounted on a common catheter. For instance, the common catheter can include a proximal shaft and a distal plurality of expandable splines, wherein first plurality of electrodes are mounted on the distal plurality of expandable splines, and wherein the second plurality of electrodes are mounted on the proximal shaft.

A first increment of ablation therapy can be applied to the tissue prior to applying the pacing signal to the tissue using a first plurality of electrodes positioned on the first side of the lesion. In some embodiments of the disclosure, the first increment of ablation therapy is applied to the tissue using a subset of the first plurality of electrodes.

According to certain aspects disclosed herein, the second plurality of electrodes can be mounted on a plurality of catheters. Electrophysiological activity in the tissue on the second side of the lesion can also be sensed on a surface electrocardiogram lead.

The pacing signal can be applied to the tissue using all of the first plurality of electrodes simultaneously. Alternatively, the pacing signal can be applied to the tissue using pairs of electrodes selected from the first plurality of electrodes sequentially. Where the pacing signal is applied using pairs of electrodes selected from the first plurality of electrodes sequentially, it is contemplated that the indicator of no conduction block can further include an indicator of a position of a gap in the lesion.

It is contemplated that the method can include delaying by a preset blanking interval between the step of applying the pacing signal to the tissue on the first side of the lesion and the step of analyzing, in the signal processor, the sensed electrophysiological activity for the response evoked by the pacing signal.

Optionally, the signal processor can also output a confidence value for the indicator of conduction block status.

The step of analyzing, in the signal processor, the sensed electrophysiological activity for the response evoked by the pacing signal can include the signal processor analyzing the sensed electrophysiological activity for a signal amplitude above a preset noise level threshold. The signal processor can use a preset noise level threshold or, alternatively, can determine the preset noise level threshold according to an amplitude of the sensed electrophysiological activity during a quiescent interval.

The instant disclosure also provides a system for assessing conduction block across a lesion in a tissue. The system includes a pacing system configured to apply a pacing signal to the tissue on a first side of the lesion, wherein the pacing signal includes a plurality of pacing pulses; a sensing system configured to sense electrophysiological activity in the tissue on a second side of the lesion, wherein the second side of the lesion is opposite the first side of the lesion; and a conduction block signal processor. The conduction block signal processor is configured to analyze the sensed electrophysiological activity for a response evoked by the pacing signal and output an indicator of conduction block status. The indictor of conduction block status can be an indicator of conduction block when a preset number of consecutive pacing pulses do not evoke the response; an indicator of no conduction block when the preset number of consecutive pacing pulses evoke the response; and an indicator of uncertain block status otherwise.

Two or more of the pacing system, the sensing system, and the conduction block signal processor may be integrated into an electroanatomical mapping system.

The system can also incorporate a multi-electrode catheter operably coupled to both the pacing system and the sensing system, wherein the multi-electrode catheter includes a first plurality of electrodes operably coupled to the pacing system to apply the pacing signal to the tissue on the first side of the lesion and a second plurality of electrodes operably coupled to the sensing system to sense the electrophysiological activity in the tissue on the second side of the lesion, and wherein the first plurality of electrodes are positioned distally of the second plurality of electrodes on the multi-electrode catheter.

The pacing system can be configured to apply the pacing signal to the tissue using each electrode of the first plurality of electrodes simultaneously.

The conduction block signal processor can be configured to determine the preset number of consecutive pacing pulses as a function of at least one of an intrinsic heartrate and a rate of the pacing signal.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for automated assessment of conduction block in tissue. For purposes of illustration, aspects of the disclosure will be described with reference to assessing conduction block resulting from a pulmonary vein isolation (PVI) procedure. Those of ordinary skill in the art will understand, however, how to apply the teachings herein to assess conduction block across other lesions, scar and low voltage regions, anatomic borders, functional blocks or delays, and the like.

Figure 1A:
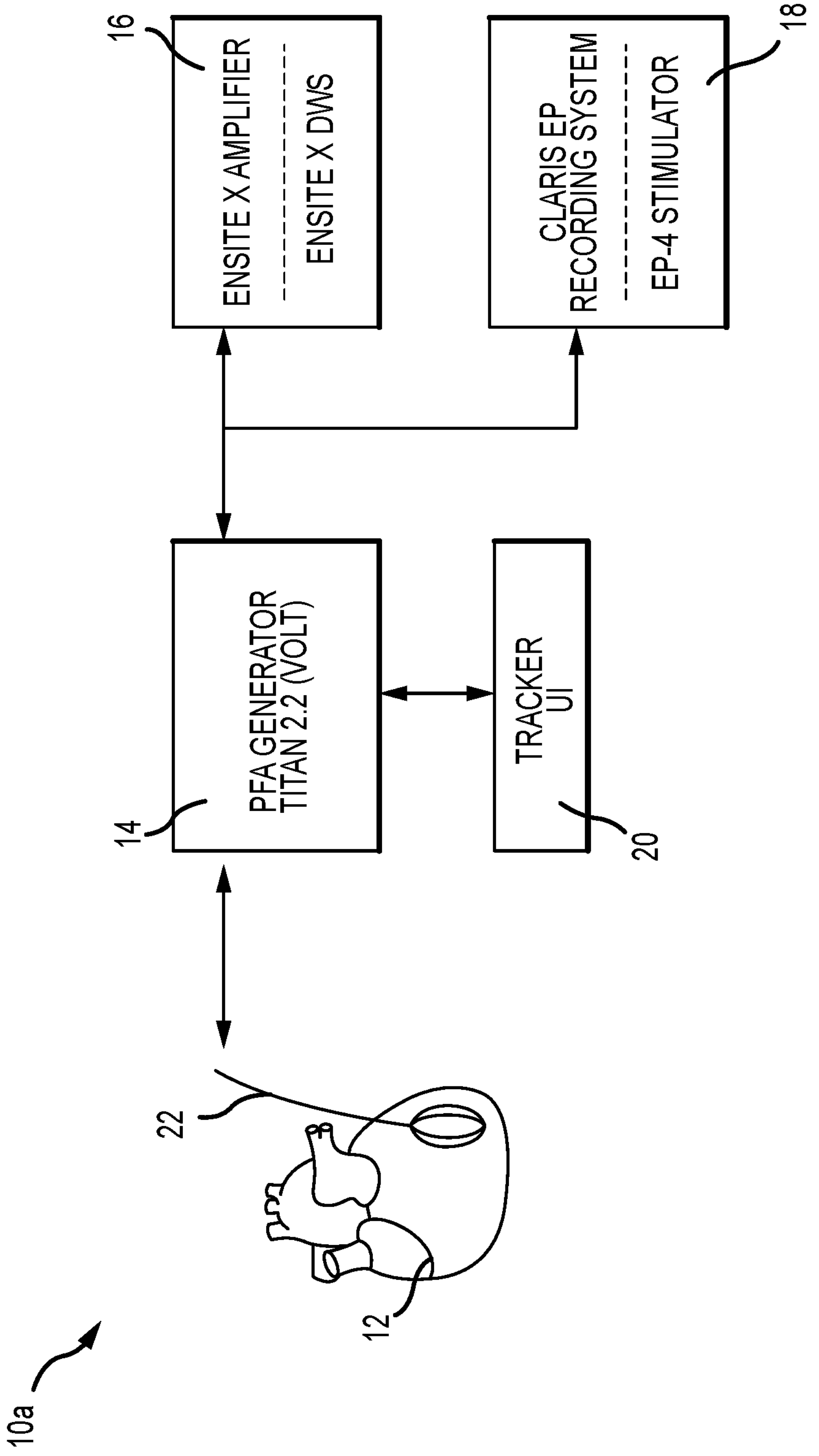
FIGS. 1A and 1B are block diagrams of systems for the assessment of conduction block according to aspects of the present disclosure.
Figure 1B:
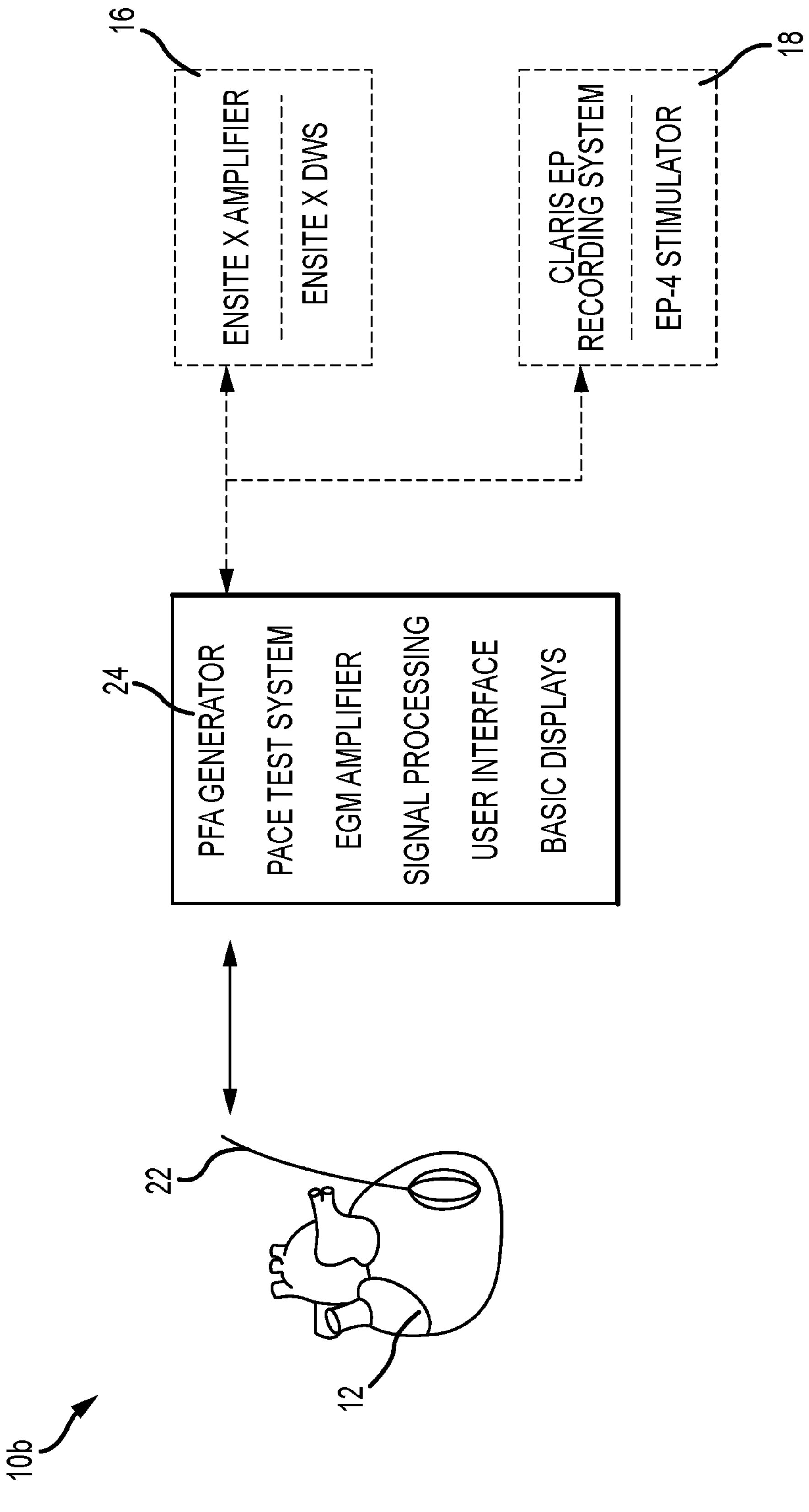

FIGS. 1A and 1B are block diagrams of exemplary systems 10 (denoted 10*a*, 10*b*, respectively) for assessing conduction block in tissue (e.g., tissue within heart 12) according to various aspects of the disclosure. More particularly, FIG. 1A illustrates an embodiment of the disclosure that interconnects various discrete hardware and software components, while FIG. 1B illustrates an embodiment of the disclosure that integrates multiple aspects described herein into a single hardware component, referred to as an ablation and test device.

As shown in FIG. 1A, system 10*a* includes an ablation generator 14. Ablation generator 14 is illustrated as a pulse field ablation (PFA) generator, but it should be understood that, insofar as it may be desirable to assess block achieved by an ablation lesion regardless of how created, other ablation modalities (e.g., radiofrequency (RF) ablation, cryogenic ablation, microwave ablation, and the like) are within the spirit and scope of the disclosure.

System 10*a* further includes an electroanatomical mapping system 16, such as the EnSite™ X, EnSite™ Velocity™, or EnSite Precision™ electrophysiological mapping and visualization system of Abbott Laboratories (Abbott Park, Illinois), and a pacing/sensing system 18, such as the WorkMate Claris™ system, which can be used in conjunction with the EP-4™ Cardiac Stimulator, both also of Abbott Laboratories. Insofar as the capabilities and operation of ablation generator 14, mapping system 16, and pacing/sensing system 18 will be familiar to those of ordinary skill in the art, they will only be described herein to the extent necessary to understand the instant disclosure.

A user interface 20 allows a practitioner to interact with, and review outputs from, system 10*a*. Additional details of user interface 20 are provided below.

Ablation generator 14, mapping system 16, and/or pacing/sensing system 18 can be operably connected to a catheter 22. A representative catheter 22 will be described in further detail below.

Those of ordinary skill in the art will further understand from the following disclosure that, although only a single catheter 22 is shown and described for purposes of illustration, the teachings herein can be applied using multiple catheters. For instance, system 10*a* can incorporate a first catheter operably connected to ablation generator 14 to deliver ablative energy to tissue within heart 12 and an additional catheter operably connected to pacing/sensing system 18 to test conduction block. As another example, system 10*a* can utilize two (or more) catheters operably connected to pacing/sensing system 18, some of which are dedicated to delivering pacing and others of which are dedicated to sensing electrophysiological activity. Indeed, in certain embodiments of the disclosure, it may be particularly desirable to use multiple catheters for sensing electrophysiological activity in heart 12.

FIG. 1B illustrates a system 10*b* that is similar to system 10*a* shown in FIG. 1A. In FIG. 1B, however, the ablation generator, pacing/sensing functionality, signal processing functionality, and the user interface are integrated into a single ablation and test device 24, which is in turn operably connected to catheter 22.

As represented by dashed lines, system 10*b* can optionally include electroanatomical mapping system 16 and/or a dedicated pacing/sensing system 18.

Figure 2:
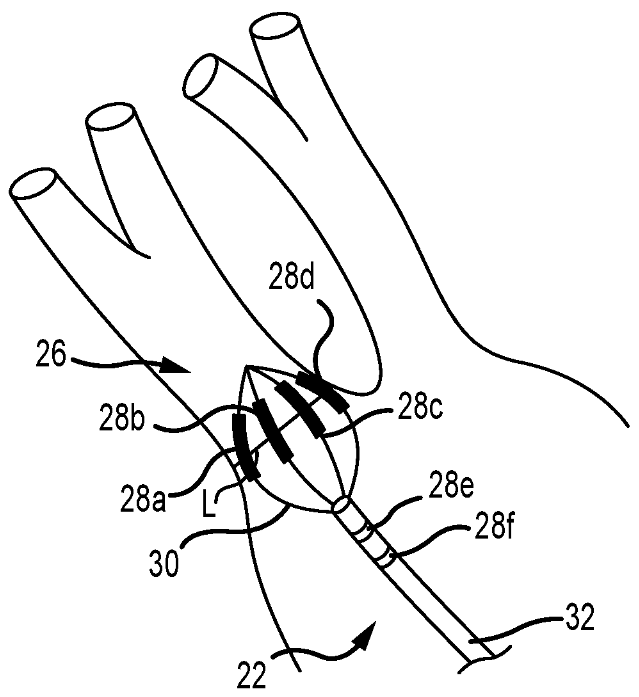
FIG. 2 depicts an exemplary catheter that can be used in connection with aspects of the instant disclosure.

FIG. 2 depicts catheter 22 positioned within heart 12 to assess conduction block across a PVI lesion in pulmonary vein 26. As shown in FIG. 2, catheter 22 includes several electrodes 28. A first plurality of electrodes 28 (those visible in FIG. 2 are designated 28*a*-28*d*, but the ordinarily-skilled artisan will appreciate that additional such electrodes 28 may be positioned on the side of catheter 22 that is not visible in FIG. 2) are mounted distally on an expandable member 30, such as a basket incorporating a plurality of splines as shown, to bring electrodes 28*a*-28*d* into contact with the wall of pulmonary vein 26. A second plurality of electrodes 28, designated 28*e* and 28*f*, are mounted proximally on shaft 32 of catheter 22.

It should be understood that the number and arrangement of electrodes 28 shown in FIG. 2 is merely exemplary. Indeed, it will become apparent from the following disclosure that variations in the number and arrangement of electrodes 28 remain within the spirit and scope of the present teachings. This includes variations where electrodes 28 are spread across two or more catheters. For example, electrodes 28*a*-28*d* can be mounted to a first catheter to be used for pacing and electrodes 28*e* and 28*f* can be mounted to a second catheter used for sensing.

Likewise, it should be understood that the particular catheter configuration shown in FIG. 2 is merely exemplary. Other suitable catheter designs include, without limitation, balloon catheters, grid catheters, linear catheters, lattice catheters, circular catheters, and spiral catheters.

Figure 3:
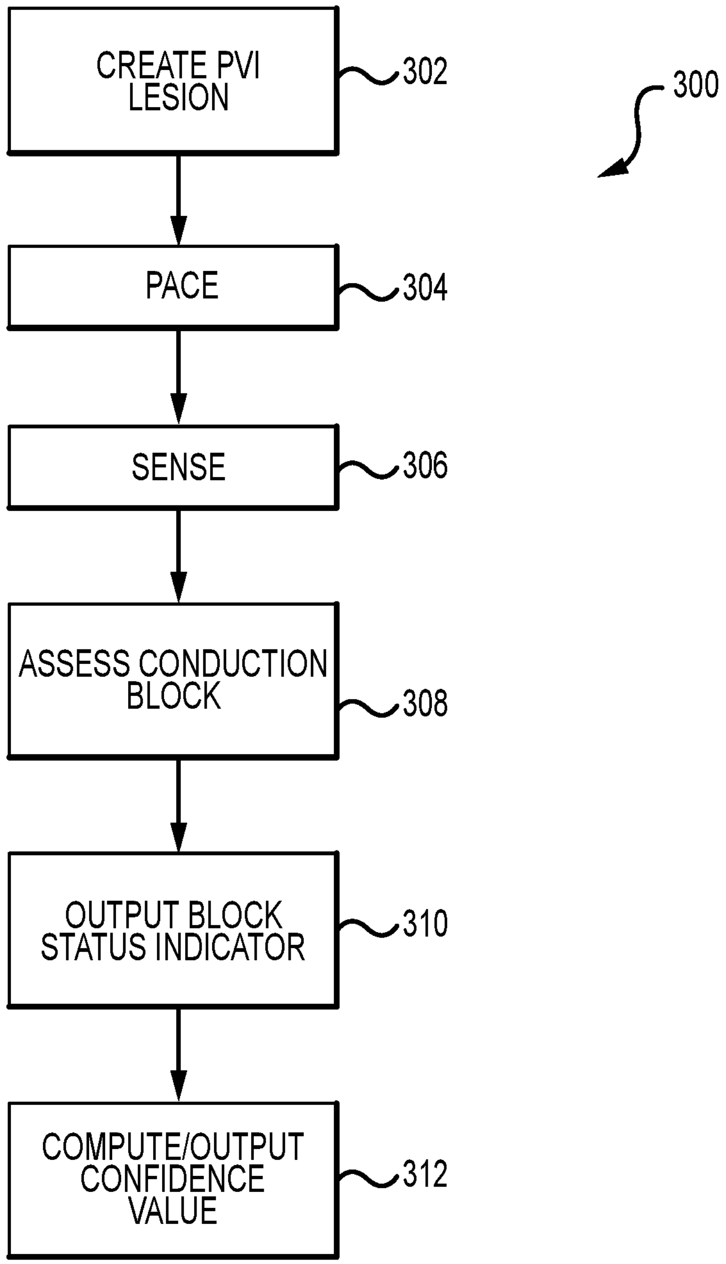
FIG. 3 is a flowchart of representative steps that can be carried out according to aspects of the instant disclosure.

Exemplary methods of assessing conduction block according to aspects of the instant disclosure will be explained with reference to the flowchart 300 of representative steps presented as FIG. 3. Flowchart 300 will first be described generally, with further details of the representative steps therein presented following the general description.

In general, flowchart 300 depicts several exemplary steps that can be carried out by system 10, and, more particularly, by one or more signal processors within system 10. As used herein, the term "signal processor" includes both hardware- and software-based processing of both analog and digital signals. Thus, the representative steps described below can be hardware-implemented, software-implemented, or implemented in a combination of hardware and software. Moreover, signal processing may occur in a single device (e.g., via a signal processor incorporated into ablation and test device 24 of system 10*b*) or may be distributed across a plurality of devices (e.g., via dedicated signal processors incorporated into ablation generator 14 and pacing/sensing system 18 of system 10*a*).

In block 302, an increment of ablation is applied to create the PVI lesion in pulmonary vein 26. In embodiments of the disclosure, ablation energy can be applied using a subset of the first plurality of electrodes 28*a*-28*d* in order to simultaneously create the entire PVI lesion (sometimes referred to as a "one shot" PVI lesion). As noted above, however, ablation may also be applied using a dedicated ablation catheter prior to inserting catheter 20 carrying electrodes 28 for conduction block assessment.

Steps 302-312 in flowchart 300 generally relate to assessing the efficacy of the PVI lesion created in block 302 in achieving conduction block. For purposes of illustration, steps 302-310 will be described with reference to assessment of exit block (that is, assessing whether the PVI lesion has interrupted the natural propagation of cardiac activation from pulmonary vein 26 to the left atrium). The ordinarily-skilled artisan will understand, however, how to adapt the teachings herein to assess entrance block and/or complete block.

In block 304, a pacing signal is applied to the tissue on a first side of the lesion (e.g., via pacing/sensing system 18 or via pacing functionality in ablation and test device 24). When assessing exit block, the upstream (distal) side of the lesion will be the first side.

In block 306, electrophysiological activity on a second side of the lesion is sensed (e.g., via pacing/sensing system 18 or via sensing functionality in ablation and test device 24). When assessing exit block, the downstream (proximal) side of the lesion will be the second side.

In block 308, a signal processor analyzes the electrophysiological activity sensed in block 306 to assess conduction block by detecting responses (if any) evoked by the pacing signal applied in block 304. As described in further detail below, if evoked responses are detected, it is likely that conduction block has not been achieved; conversely, if no evoked responses are detected, it is likely that conduction block has been achieved.

In block 310, the signal processor outputs the results of the conduction block analysis to a user as an indicator of conduction block (e.g., via user interface 20). The indicator of conduction block will typically reflect a BLOCK state, a NO BLOCK state, or an UNKNOWN (or UNCERTAIN) state.

In optional block 312, system 10 can compute and output a confidence value reflective of the probability that the analytical result reached in block 308 is correct. Further details of block 312 are discussed below.

Details of Pacing (Block 304)

In embodiments of the disclosure, the block 304 pacing signal is applied using the first plurality of electrodes 28*a*-28*d*, which, as shown in FIG. 2, are positioned on the upstream side of the lesion or directly over the lesion L. In aspects of the disclosure, the block 304 pacing signal can be applied using all of the first plurality of electrodes simultaneously within a given beat (referred to herein as "simultaneous pacing"). This can advantageously accelerate the process of assessing conduction block relative to extant (manual) approaches, which typically pace using each pair of electrodes separately and sequentially over multiple beats (referred to herein as "pairwise sequential pacing").

It is contemplated, however, that, in certain aspects of the disclosure, the block 304 pacing signal can use pairwise sequential pacing (e.g., electrodes 28*a* and 28*b*, followed by electrodes 28*b* and 28*c*, and so forth over multiple beats). Although potentially slower than simultaneous pacing at determining block status, a pairwise sequential pacing approach may enhance the ability to identify where about the circumference of pulmonary vein 26 conduction block does not exist, whereas simultaneous pacing may only be able to provide a binary BLOCK or NO BLOCK indicator result.

Indeed, it is expressly contemplated to use simultaneous pacing first, and, if NO BLOCK is detected using simultaneous pacing, to automatically switch to pairwise sequential pacing for further analysis to pinpoint the location where block does not exist.

Figure 4A:
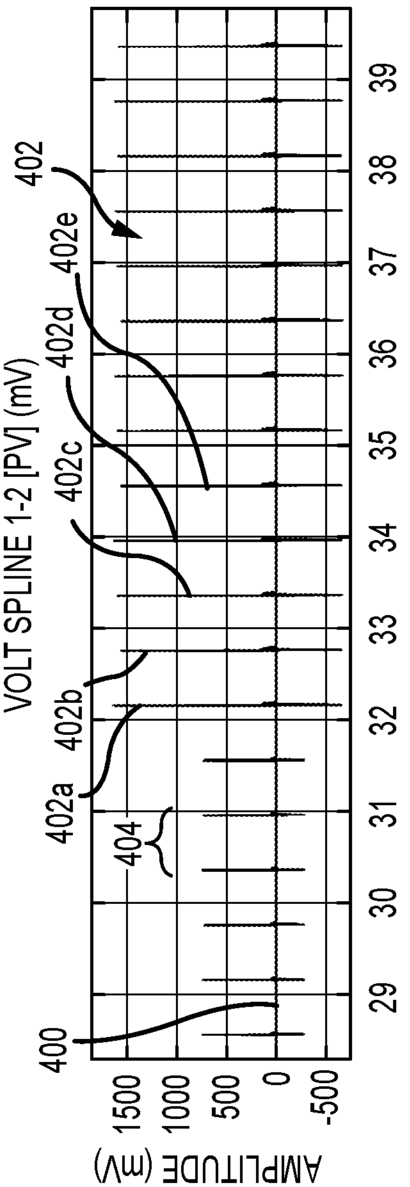
FIG. 4A is an exemplary pacing signal.

In any case, FIG. 4A depicts a representative pacing signal 400 including a plurality of pacing pulses 402 and having a cycle length 404 (that is, an interval between pacing pulses 402). In order to minimize the likelihood that natural activation of tissue will be mistaken for an evoked response in sensing step 306, the cycle length 404 of pacing signal 400 is set to minimize the chance of N-of-M pacing (that is, pacing at the intrinsic cycle length or a multiple thereof). Thus, pacing signal 400 can have a preset cycle length 404 that is slightly less than a typical intrinsic cycle length, such as between about 500 ms and about 600 ms.

It is contemplated that system 10 can be programmed to alert a user if the preset cycle length 404 should be adjusted. Indeed, in certain embodiments of the disclosure, if the preset cycle length 404 is not set appropriately, system 10 can suspend analysis block 308 and/or indication block 310 until the user adjusts it to a suitable value.

It is also contemplated that cycle length 404 of pacing signal 400 can be determined from patient-specific electrophysiological data. For instance, the patient's intrinsic cycle length can be measured (e.g., during sinus rhythm or during subthreshold pacing) using surface electrocardiograms (ECG) and/or intracardiac electrograms (EGM) according to methods that will be familiar to those of ordinary skill in the art. Once the intrinsic cycle length is measured, the cycle length 404 of pacing signal 400 can be set at a value that is slightly different from the intrinsic cycle length, such as about 60% to about 90% of the intrinsic cycle length or about 100 ms to about 400 ms less than the intrinsic cycle length.

Further, and in addition to considering intrinsic cycle length when determining cycle length 404 of pacing signal 400, system 10 can consider the length of the atrioventricular interval.

The ordinarily-skilled artisan will also appreciate the relationship between a suitable cycle length 404 of pacing signal 400 and the length of the preset analysis interval (discussed in greater detail below).

Those of ordinary skill in the art will also appreciate that the amplitude and duration (width) of each pulse 402 within pacing signal 400 should be sufficient to capture the tissue being paced while avoiding far field capture. By way of example only, embodiments of the disclosure use a preset amplitude of about 5 mA and a preset width of about 2 ms.

In other embodiments of the disclosure, the amplitude and width of each pulse 402 can be determined from patient-specific electrophysiological data, such as ECG and/or EGM signals taken during the procedure. As one example, prior to the creation of a PVI lesion (e.g., prior to step 302), one would expect the conduction block assessment process described herein (e.g., steps 304-310) to yield a NO BLOCK result. If, instead, it produces a pre-ablation BLOCK result, it is likely that the amplitude and/or width of pulse 402 is too small to capture the tissue. This suggests that the amplitude and/or width of pulse 402 should be increased for post-ablation conduction block assessment (e.g., after step 302).

As another example, if far field capture is suspected of causing a (false) NO BLOCK result post-ablation, it may be desirable to reduce the amplitude of pulse 402, thus minimizing the possibility of block 304 pacing causing far field capture and yielding erroneous NO BLOCK results.

Details of Sensing (Block 306)

Figure 4B:
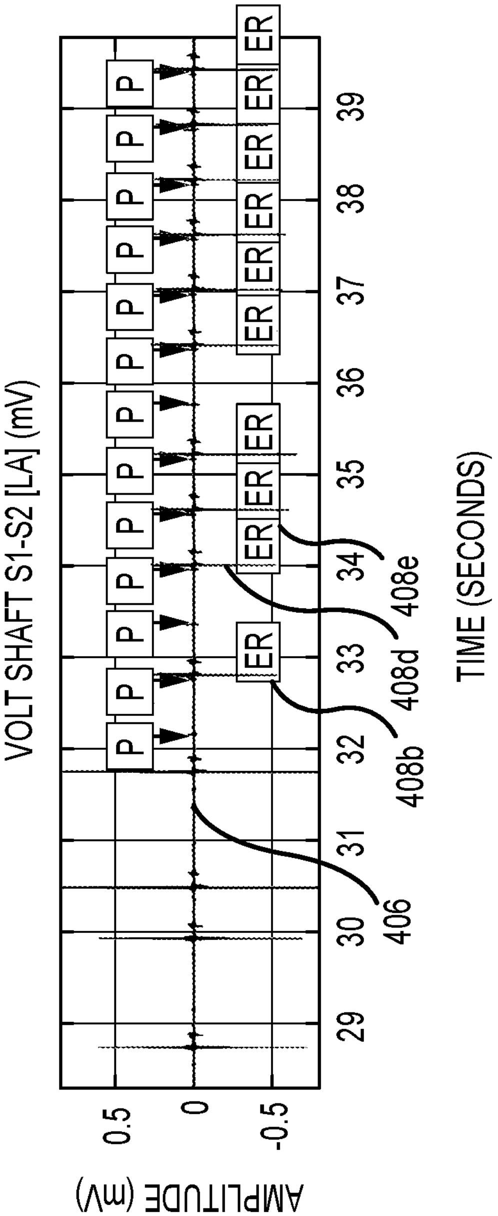
FIG. 4B is an exemplary sensed electrophysiological activity signal responsive to the pacing signal shown in FIG. 4A.

In embodiments of the disclosure, electrodes 28*c*, 28*f*, which as shown in FIG. 2 are positioned on the downstream side of the lesion, are used to sense bipolar electrograms. FIG. 4B depicts a representative bipolar electrogram 406 sensed in block 306 by electrodes 28*c*, 28*f*. Within this electrogram 406, and to aid the reader in understanding this disclosure, pacing pulses 402 are annotated in FIG. 4B with "P" and evoked responses (vertical lines extending downward to about −0.5 mV) are annotated with "ER."

Other approaches to sensing electrophysiological activity in the tissue are contemplated, however. For example, an additional catheter, (e.g., a high density (HD) grid catheter, such as the Advisor™ HD Grid Mapping Catheter, Sensor Enabled™, from Abbott Laboratories), can be used to sense omnipolar electrograms from within the left atrium. United States patent application publication no. 2018/0296111, which is hereby incorporated by reference as though fully set forth herein, describes the computation of omnipolar electrograms.

In other embodiments of the disclosure, electrophysiological activity can be sensed using a catheter positioned in the coronary sinus. Surface ECG signals may also be employed to good advantage in sensing block 306.

Combinations of the foregoing are also contemplated. For instance, electrophysiological activity can be sensed using both electrodes 28*c*, 28*f* and a surface ECG, or using both electrodes 28*c*, 28*f* and an HD grid catheter within the left atrium.

Details of Analysis (Block 308)

In block 308, system 10 analyzes the electrophysiological activity sensed in block 306 (e.g., signal 406) to detect responses evoked by pacing signal 400. To minimize the possibility of detecting an upstream pacing artifact, rather than an evoked response, a preset blanking interval (e.g., about 20 ms) of signal 406 following each pacing pulse 402 is not analyzed for evoked responses; rather, only a preset analysis interval (e.g., about 80 ms) of signal 406 following the preset blanking interval is analyzed for evoked responses.

System 10 can detect evoked responses by looking for amplitude peaks in signal 406 that exceed a noise level threshold. In embodiments of the disclosure, the noise threshold is preset to between about 0.03 mV and about 0.04 mV.

In other embodiments of the disclosure, the noise level threshold can be determined from procedure-specific electrophysiological data, such as ECG and/or EGM signals taken during the procedure. For instance, the baseline noise signal can be identified within an EGM signal taken during the procedure (e.g., during quiescent intervals between beats), and the amplitude of the baseline noise signal can be used as the noise level threshold (or, alternatively, to determine the noise level threshold, such as by setting the noise threshold slightly above the amplitude of the baseline noise signal).

Other approaches to detecting evoked responses in block 308 are contemplated. For example, rather than detecting evoked responses based on the amplitude of signal 406, system 10 can employ other signal characteristics including, but not limited to: the absolute value of signal 406, the square of signal 406, the root mean square of signal 406, the peak frequency of signal 406, the first derivative of signal 406 with respect to time, and various energy-based methods. It may also be desirable to filter signal 406 prior to analysis (e.g., using a bandpass filter that passes frequencies between about 30 Hz and about 300 Hz).

As mentioned, system 10 assesses conduction block status by evaluating signal 406 for responses evoked by pacing pules 402, and makes the determination of conduction block status when it detects at least a preset number of identical, consecutive results. In certain embodiments of the disclosure, the preset number is two. It should be understood, however, that this is merely exemplary; higher numbers of identical, consecutive results can increase confidence in the conduction block status determination reached in block 308, but will likewise increase the time necessary to reach such a determination. For instance, in some embodiments of the disclosure, the preset number of identical, consecutive results can be user adjustable. As another example, in additional embodiments of the disclosure, system 10 can determine the preset number of identical, consecutive results analytically, as a function of the intrinsic heartrate and/or the pacing rate.

If system 10 does not detect any evoked responses in signal 406 over the preset number of consecutive pacing pulses 402, then system 10 can determine that conduction block has been achieved. On the other hand, if system 10 detects evoked responses in signal 406 over the preset number of consecutive pacing pulses 402, then system 10 can determine that conduction block has not been achieved. Otherwise (e.g., until the requisite number of consecutive pacing pulses 402 yield identical results), system 10 will remain in an unknown block status.

As an example, consider again FIGS. 4A and 4B. System 10 begins in an UNKNOWN state. No evoked response is seen in signal 406 after pulse 402*a* (shortly after 32 sec), but system 10 necessarily remains in an UNKNOWN state following first pulse 402*a*. Pulse 402*b* (shortly before 33 sec) does evoke a response 408*b*, but, because it is an evoked response following no evoked response, system 10 remains in an UNKNOWN state. Pulse 402*c* (shortly after 33 sec) once again does not evoke a response in signal 406; once again, because there have not been two consecutive identical results, system 10 remains in an UNKNOWN state.

The next two pulses 402*d*, 402*e* (at about 34 s and at about 34.5 s, respectively) evoke responses 408*d*, 408*e*, respectively, in signal 406. Because evoked response 408*d* follows no evoked response, system 10 remains in an UNKNOWN state after pulse 402*d*. On the other hand, because evoked response 408*e* is the second consecutive evoked response, system 10 moves to a NO BLOCK state after pulse 402*e* and analysis can cease.

System 10 may also incorporate additional analysis to minimize system 10 mistaking intrinsic atrial depolarizations and far-field R-waves for evoked responses. In particular, evoked responses should occur with relatively consistent timing following pacing pulses 402. False evoked responses, such as intrinsic depolarizations and far-field signals or excessively low output pacing, will not exhibit the same degree of consistency, particularly for pacing cycle lengths 404 that are similar to the intrinsic cycle length.

In embodiments of the disclosure, therefore, system 10 will also check the timing of an apparent evoked response ER relative to the timing of pacing pulse P to verify that it is occurring within a preset expected time window (e.g., the apparent evoked response ER follows the pacing pulse P by no more than a preset duration) before concluding that it is, in fact, an evoked response.

Details of Indicator Output (Block 310)

In block 310, system 10 outputs (e.g., through user interface 20) a BLOCK, NO BLOCK, or UNKNOWN indicator to alert a user to the results of the analysis in block 308. The indicator can be visual (e.g., output to a display within system 10, such as may be part of electroanatomical mapping system 16, ablation and test device 24, or user interface 20), audible (e.g., a tone can sound when BLOCK is achieved), and/or haptic (e.g., the handle of catheter 22 can vibrate when BLOCK is achieved).

There are various approaches to visual indicators of block status that a practitioner may find useful or desirable in connection with the present teachings. For instance, in some embodiments of the disclosure, a straightforward text-based annotation (e.g., the term "BLOCK" or the phrase "NO BLOCK") and/or color code (e.g., coloring sensed signal 406 or another signal trace, coloring a graphical representation of catheter 20, or displaying a "traffic light," where yellow indicates UNKNOWN, green indicates BLOCK, and red indicates NO BLOCK) may be output to user interface 20.

Figure 5B:
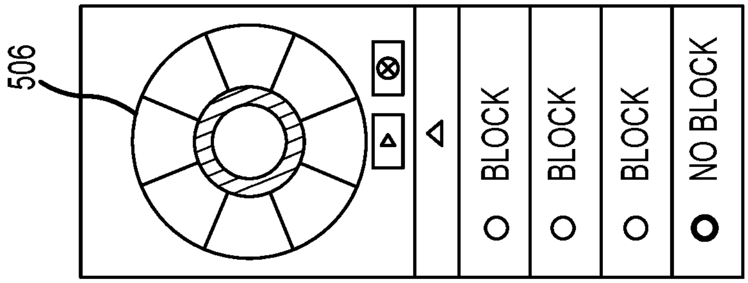
FIGS. 5A and 5B illustrate block status indicators according to embodiments disclosed herein.
Figure 5A:
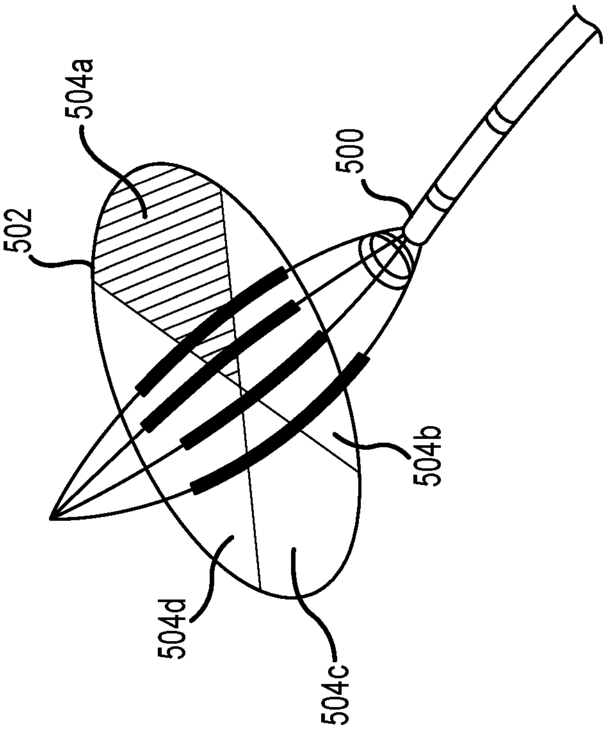

FIG. 5A depicts a visual indicator of block status that may be particularly advantageous in connection with pairwise sequential pacing. In particular, a three-dimensional depiction 500 of catheter 20 is presented with a surrounding fan-shaped indicator 502. Indicator 502 is divided into sectors 504*a*-504*d* generally corresponding to the sequential pairs of electrodes 28*a*-28*d* used for pacing. These sectors 504*a*-504*d* can be selectively illuminated, shaded, or otherwise highlighted to indicate that they correspond to regions of NO BLOCK.

Indicator 502 can also be used for simultaneous pacing. In this case, rather than selectively illuminating, shading, or otherwise highlighting individual sectors 504*a*-504*d*, the entirety of indicator 502 can be illuminated, shaded, or otherwise highlighted in a NO BLOCK state.

As an alternative to a separate fan-shaped indicator 502, the three-dimensional depiction 500 of catheter 20 (or portions thereof) can be selectively illuminated, shaded, or otherwise highlighted to indicate NO BLOCK status and/or orientation. Likewise, the three-dimensional model of heart 12 could be selectively illuminated, shaded, or otherwise highlighted to indicate NO BLOCK status and/or location.

In still other alternatives, the three-dimensional depiction 500 and/or indicator 502 of FIG. 5A can be replaced with a more compact two-dimensional indicator 506, for example as shown in FIG. 5B. Of course, indicator 506 can also be divided into sectors in order to provide region-specific NO BLOCK indicators.

Confidence Values

As mentioned above, in optional block 312, system 10 can compute and output a confidence value reflective of the probability that the analytical result reached in block 308 is correct (e.g., that a determination of BLOCK is not a false positive, for example because pacing signal 400 was insufficient to capture tissue, or that a determination of NO BLOCK is not a false negative, for example because the detection in signal 406 is far field activity rather than an evoked response).

Various factors can raise or lower the confidence value. For example, the confidence value can increase with every additional consecutive, consistent result (e.g., consecutive BLOCK or NO BLOCK results) and decrease if successive results are inconsistent.

As another example, the confidence value in a NO BLOCK result can increase as the amplitude of the post-pacing response in signal 406 further exceeds the noise threshold. That is, the closer the amplitude of the post-pacing response in signal 406 is to the noise threshold, the more likely it is noise, and thus the lower the confidence value should be.

As still another example, the confidence value can decrease the closer the post-pacing response in signal 406 is to the edge of the analysis interval. That is, the closer the post-pacing response in signal 406 is to the edge of the analysis interval, the more likely it is an artifact rather than an evoked response, and thus the lower the confidence value should be.

Relatedly, and similar to the discussion above regarding approaches that can be used to avoid mistaking intrinsic atrial depolarizations, far-field R-waves, and other signals for evoked responses, the consistency of the timing between the pacing pulse and the evoked response can contribute to the confidence value.

In yet a further example, the suitability or appropriateness of the preset cycle length 404 of pacing signal 400 can contribute to the confidence value.

System 10 can also output a graphical representation of the confidence value. For example, the brightness or intensity of the illumination of a "traffic light" indicator can increase with increasing confidence. Conversely, if the confidence is below a preset threshold, the display may remain in the UNKNOWN state despite a marginal determination otherwise.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to data collected during an electrophysiology study performed at an earlier time).

As another example, techniques to assess contact between electrodes 28 and tissue, such as those based on impedance sensing, can be employed to ensure suitable contact prior to initiating pacing in block 304.

As yet another example, although an illustrative embodiment is described above with reference to a first plurality of electrodes to apply a pacing signal on the first side of a lesion and a second plurality of electrodes to sense electrophysiological activity on the second side of the lesion, either or both of the first and second pluralities of electrodes could be replaced by a single electrode (e.g., a single pacing electrode on the first side of the lesion and/or a single sensing electrode on the second side of the lesion).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of assessing conduction block across a lesion in a tissue, comprising:

applying a pacing signal to the tissue on a first side of the lesion, wherein the pacing signal comprises a plurality of pacing pulses;

sensing electrophysiological activity in the tissue on a second side of the lesion, wherein the second side of the lesion is opposite the first side of the lesion;

analyzing, in a signal processor, the sensed electrophysiological activity for a response evoked by the pacing signal;

outputting, via the signal processor, an indicator of conduction block status, wherein the indicator of conduction block status comprises:

an indicator of conduction block when a preset number of consecutive pacing pulses do not evoke the response;

an indicator of no conduction block when the preset number of consecutive pacing pulses evoke the response; and an indicator of uncertain block status otherwise.

2. The method according to claim 1, wherein:

applying the pacing signal to the tissue on the first side of the lesion comprises applying the pacing signal to the tissue using a first plurality of electrodes positioned on the first side of the lesion; and sensing electrophysiological activity in the tissue on the second side of the lesion comprises sensing the electrophysiological activity using a second plurality of electrodes positioned on the second side of the lesion.

3. The method according to claim 2, wherein the first plurality of electrodes and the second plurality of electrodes are mounted on a common catheter.

4. The method according to claim 3, wherein the common catheter comprises a proximal shaft and a distal plurality of expandable splines, wherein first plurality of electrodes are mounted on the distal plurality of expandable splines, and wherein the second plurality of electrodes are mounted on the proximal shaft.

5. The method according to claim 3, further comprising applying a first increment of ablation therapy to the tissue prior to applying the pacing signal to the tissue using a first plurality of electrodes positioned on the first side of the lesion.

6. The method according to claim 5, wherein applying the first increment of ablation therapy to the tissue comprises applying the first increment of ablation therapy to the tissue using a subset of the first plurality of electrodes.

7. The method according to claim 2, wherein the second plurality of electrodes are mounted on a plurality of catheters.

8. The method according to claim 2, wherein applying the pacing signal to the tissue using a first plurality of electrodes positioned on the first side of the lesion comprises applying the pacing signal to the tissue using all of the first plurality of electrodes simultaneously.

9. The method according to claim 2, wherein applying the pacing signal to the tissue using a first plurality of electrodes positioned on the first side of the lesion comprises applying the pacing signal to the tissue using pairs of electrodes selected from the first plurality of electrodes sequentially.

10. The method according to claim 9, wherein the indicator of no conduction block further comprises an indicator of a position of a gap in the lesion.

11. The method according to claim 2, wherein sensing electrophysiological activity in the tissue on the second side of the lesion further comprises sensing the electrophysiological activity using a surface electrocardiogram lead.

12. The method according to claim 1, further comprising delaying by a preset blanking interval between the step of applying the pacing signal to the tissue on the first side of the lesion and the step of analyzing, in the signal processor, the sensed electrophysiological activity for the response evoked by the pacing signal.

13. The method according to claim 1, wherein the indicator of conduction block status comprises one or more of a visual indicator of conduction block status; an audible indicator of conduction block status; and a haptic indicator of conduction block status.

14. The method according to claim 1, further comprising outputting, via the signal processor, a confidence value for the indicator of conduction block status.

15. The method according to claim 1, wherein the step of analyzing, in the signal processor, the sensed electrophysiological activity for the response evoked by the pacing signal comprises the signal processor analyzing the sensed electrophysiological activity for a signal amplitude above a preset noise level threshold.

16. The method according to claim 15, wherein the signal processor determines the preset noise level threshold according to an amplitude of the sensed electrophysiological activity during a quiescent interval.

17. A system for assessing conduction block across a lesion in a tissue, comprising:

a pacing system configured to apply a pacing signal to the tissue on a first side of the lesion, wherein the pacing signal comprises a plurality of pacing pulses;

a sensing system configured to sense electrophysiological activity in the tissue on a second side of the lesion, wherein the second side of the lesion is opposite the first side of the lesion; and a conduction block signal processor configured to:

analyze the sensed electrophysiological activity for a response evoked by the pacing signal; and output an indicator of conduction block status, wherein the indicator of conduction block status comprises:

an indicator of conduction block when a preset number of consecutive pacing pulses do not evoke the response;

an indicator of no conduction block when the preset number of consecutive pacing pulses evoke the response; and an indicator of uncertain block status otherwise.

18. The system according to claim 17, wherein the pacing system, the sensing system, and the conduction block signal processor are integrated into an electroanatomical mapping system.

19. The system according to claim 17, further comprising a multi-electrode catheter operably coupled to both the pacing system and the sensing system, wherein the multi-electrode catheter comprises a first plurality of electrodes operably coupled to the pacing system to apply the pacing signal to the tissue on the first side of the lesion and a second plurality of electrodes operably coupled to the sensing system to sense the electrophysiological activity in the tissue on the second side of the lesion, and wherein the first plurality of electrodes are positioned distally of the second plurality of electrodes on the multi-electrode catheter.

20. The system according to claim 19, wherein the pacing system is configured to apply the pacing signal to the tissue using each electrode of the first plurality of electrodes simultaneously.

21. The system according to claim 17, wherein the conduction block signal processor is further configured to determine the preset number of consecutive pacing pulses as a function of at least one of an intrinsic heartrate and a rate of the pacing signal.

* * * * *